United States Patent [19]

Roos

[11] 3,945,800
[45] Mar. 23, 1976

[54] APPARATUS FOR COMBINED PROTECTION AGAINST NUCLEAR FALLOUT AND NUCLEAR SUFFOCATION

[76] Inventor: Charles J. Roos, 1832 E. Isabella Ave., Muskegon, Mich. 49442

[22] Filed: July 13, 1972

[21] Appl. No.: 271,515

[52] U.S. Cl.......... 23/232 R; 52/169 R; 116/114 R; 431/345
[51] Int. Cl.² ..................... G01N 31/12; E04H 9/00
[58] Field of Search........ 116/114 R, 114 N, 114 Y, 116/114 P, 114 F; 52/167, 169, 184; 73/23 R; 431/345; 23/232 R, 254 R; 98/29, 31, 50; 128/145 A

[56] References Cited
UNITED STATES PATENTS

| | | | |
|---|---|---|---|
| 1,027,823 | 5/1912 | Davis | 23/232 R |
| 1,296,499 | 3/1919 | Fether | 116/114 F |
| 2,728,212 | 12/1955 | Costello | 431/345 X |
| 2,822,765 | 2/1958 | Rudinger | 52/184 X |
| 3,138,944 | 6/1964 | Gauthier | 431/345 X |
| 3,208,410 | 9/1965 | Hayes et al. | 52/169 X |

OTHER PUBLICATIONS
Publication: "Dacor Snorkels," Dive Dacor, 1973, 5-21-1973.
Publication: "The Haldane Flame-Test Apparatus" by J. S. Haldane, Sibe, Gorman & Co., Ltd. - G. Britain Mfgrs., 9/30/12, pp. 1-4.

Primary Examiner—Richard C. Queisser
Assistant Examiner—Daniel M. Yasich
Attorney, Agent, or Firm—Price, Heneveld, Huizenga & Cooper

[57] ABSTRACT

A method and apparatus for protecting human beings from the combined aftereffects of a nuclear explosion, namely, penetrating radiation and the settling of carbon dioxide in low areas. A warning barrier of rope or cord with newspaper suspended therefrom is erected in the upper level of a building to delineate a safe area beyond the penetration distances of alpha and beta radiation. A combustion means having an exposed flame is provided within the safe area for insertion through an aperture in the floor into the basement of the building where refuge is to be sought against more penetrating gamma radiation. The flame is observed through a second aperture to check and verify the quality of the atmosphere therein before entering the basement.

6 Claims, 6 Drawing Figures

APPARATUS FOR COMBINED PROTECTION AGAINST NUCLEAR FALLOUT AND NUCLEAR SUFFOCATION

This invention relates to a method and apparatus for the protection of human beings in the event of a nuclear attack. More particularly, it relates to a method and apparatus for the protection against the hazards of nuclear radiation and the accumulation of unbreathable gases accompanied by the reduction of oxygen in certain portions of the atmosphere in the event of a nuclear explosion.

BACKGROUND OF THE INVENTION

A nuclear explosion poses a multitude of problems to human existence. Subsequent to the initial shock waves and the incendiary effects of the initial heat waves, the combined effects of nuclear fallout and the settling of unbreathable, heavier-than-air gases in low areas surrounding the explosion produce great risks for humans inhabiting those areas. Primarily, such unbreathable gases comprise large quantities of carbon dioxide generated by the massive conflagration created by the explosion.

Nuclear radiation is produced by the spontaneous nuclear decay and transformation of materials and elements exposed to the nuclear explosion. The process of decay or transformation emits great amounts of energy in the form of alpha, beta or gamma rays. This energy-emitting process is termed "radioactivity," and, depending on the energy and/or wave length of the particular wave or ray involved, human exposure to radioactivity causes varying degrees of sickness and even death.

Alpha rays are produced by the spontaneous emission of helium nuclei from radioactive elements. A continuous stream of such helium nuclei forms the alpha ray. The alpha particles forming the alpha ray are easily dissipated by thin layers of shielding such as a few centimeters of air or less than a millmeter of aluminum. Without shielding the rays do not penetrate beyond the superficial layers of the skin.

A beta ray is a continuous stream of electrons emitted from a radioactive or decaying atomic nucleus. Since an electron has a much smaller mass than a helium nucleus, the beta particles forming the beta ray have a much smaller mass than the alpha particles forming the alpha ray. Due in part to this smaller mass, beta rays can penetrate somewhat further than alpha rays, but in any event may be stopped by a few millimeters of lead or other dense material or a somewhat greater amount of air than is required to absorb alpha rays. Even without shielding, beta rays would be absorbed in the outer layers of skin and would not reach internal organs.

Gamma rays are not formed by the emission of small particles of mass, but are extremely penetrating electromagnetic radiation having extremely short wave lengths and high energy. Gamma rays also originate in the atomic nucleus and usually accompany alpha and beta emission. A great deal of shielding is necessary to absorb gamma rays. The highest energy gamma rays will even penetrate several centimeters of lead shielding. However, gamma rays can be absorbed by sufficient thicknesses of concrete and earth as well as by sufficient thicknesses of lead. Without shielding, gamma rays do great harm to the human body since they penetrate the body affecting internal organs and bones. Thus, although alpha and beta rays may be completely dissipated by several feet of air and/or an intermediate layer of another material, gamma rays, and especially high energy gamma rays, require significantly greater thicknesses of shielding materials.

In order to avoid such radiation, people would move into their basements. This, however, exposes them to a second danger. After a nuclear explosion, the heat and incendiary effects of the explosion produce great amounts of carbon dioxide. Carbon dioxide is heavier than air and thus will settle in depressions and low spots, such as basements, in the areas surrounding the blast. Since carbon dioxide is tasteless, colorless and odorless, there is little or no warning to persons who take shelter from radiation effects in cellars, basements or other low protected area. In this connection, it is well to realize that the basement of an individual dwelling will provide the greatest protection against the highly penetrating gamma rays due to the thicknesses of the walls and earth surrounding the house. Consequently, the escape from radioactivity may end in suffocation.

SUMMARY OF THE INVENTION

Accordingly, it is an object of the present invention to provide a method and apparatus for protecting human beings against the combined aftereffects of a nuclear explosion, both radiation buildup and carbon dioxide buildup. This object is not in a way that is convenient and with materials which are inexpensive and readily available to all.

In one form of the invention, the method comprises erecting a warning barrier on an upper level of the building around the perimeter of an area within the building which is beyond the penetration distances of prolonged nuclear radiation, particularly alpha and beta radiation, following a nuclear explosion. If people are forced out of a stench filled, carbon dioxide filled basement, the warning barrier serves to keep them within safer areas of the floor to which they have been forced. To determine when it might be safe to return to the basement, means are disposed within the confines of the warning barrier for determining the amount of oxygen present within the lower level of such a building.

The warning barrier erected within the building may take the form of ropes of cords suspended between the wall of a building from hooks fastened to the walls at predetermined positions thereon. Colored newspapers or other papers may be hung from the cord or rope to provide a clear differentiation between the protected and unprotected areas defined by the warning barrier.

Preferably, the method for determining the amount of oxygen present within a building comprises the steps of providing a portable combustion means, inserting the combustion means into desired areas of the atmosphere within the building, and probing the atmosphere with the portable combustion means such that the amount of oxygen present therein may be visually determined.

In another aspect of the invention, the apparatus employed comprises a portable combustion means having at least one flame exposed to the atmosphere, the combustion means also including an elongated extension projecting therefrom for probing various areas from remote positions away from those areas. One embodiment of the combustion means comprises an elongated conduit reciprocally mounted in the floor between the upper and lower levels of the building. The conduit has a flow of combustible gas passing therethrough and ignited in a flame at the end of the conduit. The conduit may then be lowered through the floor into the lower level of the building and visually checked to determine whether a sufficient amount of oxygen is present in the lower level to sustain the flame at the end of the conduit. As is apparent, if there is enough oxygen to sustain the flame, there is enough to sustain human life. Another form of the combustion means comprises a self-contained torch such as a blowtorch or butane torch which is fastened to an extended handle and may be used by persons entering the lower levels to probe the various areas of the lower levels to search for areas containing a sufficient amount of oxygen.

These and other objects, advantages and features of the invention will become apparent from a study of the following description taken in conjunction with the drawings.

DESCRIPTION OF THE PREFERRED EMBODIMENT

Figure 1:
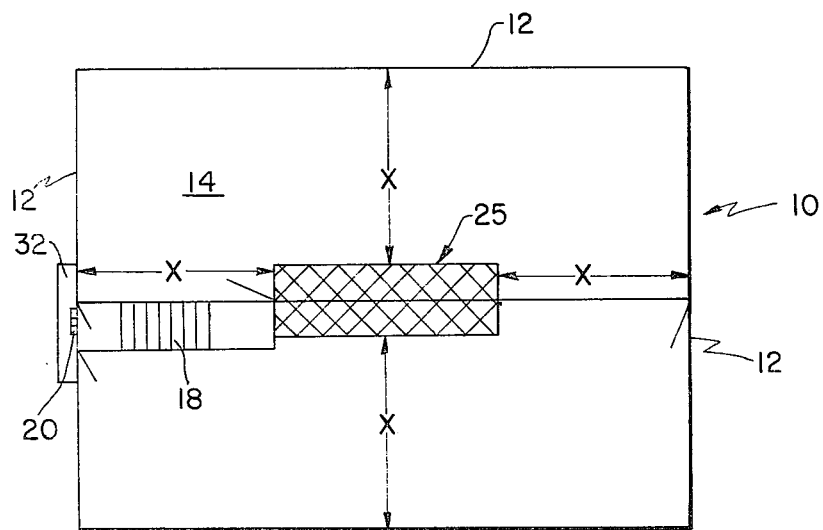
FIG. 1 is a plan view of one floor of a typical house or dwelling including the area within that dwelling which is safe from nuclear radiation and defined by the warning barrier comprising a portion of this invention.
Figure 2:
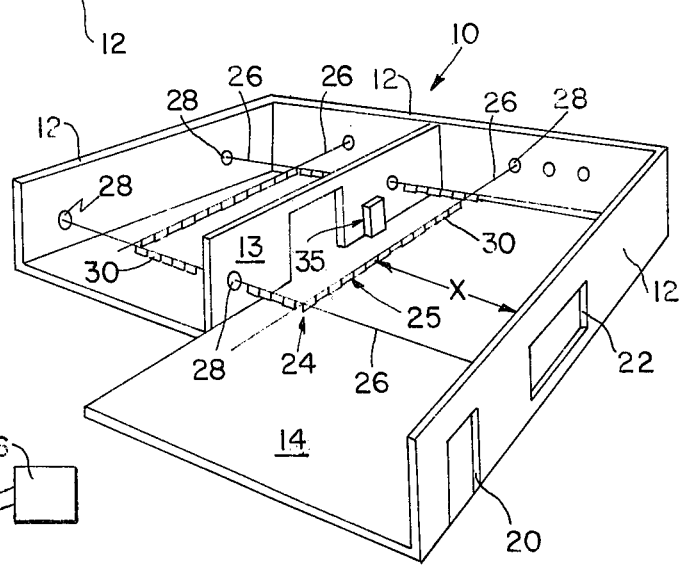
FIG. 2 is a fragmentary perspective view of a typical dwelling such as that shown in FIG. 1 including the warning barrier suspended from the walls thereof.

As described above, the aftereffects of a nuclear explosion will require precautions on the part of individuals living within the blast area if they are to survive. Since most persons within the area will be living in a house, dwelling, apartment or other structure having at least two levels comprising an upper and lower level, a typical house or dwelling 10, such as that shown in FIGS. 1 and 2, is taken as the basis for providing the subject of this invention. It should be noted that such a dwelling provides protection in various portions thereof for all types of radiation encountered following a nuclear explosion. In this respect, certain areas of the upper floors of such a dwelling 10 provide protection for the alpha and beta rays since, as mentioned above, such rays are dissipated in relatively short distances. The typical dwelling 10 can also provide protection in its basement or cellar areas 16 from gamma radiation. Thus, the typical cellar will have walls of concrete surrounded by several cubic yards of earth. If one enters such a basement and crouches low along the basement walls, he is provided with sufficient protection from gamma rays emanating from sources several miles distant. Protection is afforded since the gamma rays travel approximately parallel to the ground and over his head or are absorbed by the concrete and earth between himself and the source of the gamma rays. Thus, the typical housing unit can provide the required radiation protection if sufficient precautions are taken before entering the various portions of the dwelling to determine whether or not the atmosphere in those areas is sufficient to support life.

In reference to FIGS. 1 and 2, there is shown in dwelling 10 a protected or safe area 25 which is outside or beyond the penetration range or distances of most of the nuclear radiation following a nuclear explosion. As described above, alpha and beta radiation is produced by nuclear fallout and thus all houses or dwelling units within a blast area could be showered with such fallout. At worse, such fallout could coat the exterior of the typical house or dwelling 10. Given such a coating of fallout, which fallout produces alpha and beta radiation, the dwelling 10 on its upper level can still provide radiation protection within the defined protected or safe area shown at 25. This area is an area spaced a predetermined distance beyond or within the exterior walls 12 of the dwelling 10. Typically, the predetermined distance, represented by "X" in FIGS. 1 and 2, includes the dissipation distance for alpha and beta radiation of the highest energy level plus an additional safety margin.

The safety margin is easily calculated by those familiar with nuclear radiation from nuclear engineering texts and other books showing dissipation distances of radiation of various energies in various materials. Depending on the density composition of the external walls 12 of the house 10, the safety margin is larger or smaller. Thus, in a house having walls 12 of a high density, the safety margin is accordingly less and vice versa for a house having lower density walls. In the preferred embodiment, the distance "X" is approximately 10 feet within the exterior walls 12 of dwelling 10.

The method of differentiating the safe or protected area 25 from the remainder of the house which is unsafe or not protected comprises erecting a warning barrier 24 by suspending ropes 26 between the exterior walls 12 or exterior and interior walls 12 and 13, respectively, by means of prepositioned hooks or other securing means 28. The hooks 28 are located at the required positions prior to any nuclear attack such that, in the event of a nuclear explosion, and in the event that the house or dwelling 10 remains intact after the expolsion, lengths of rope or cord 26 are quickly and easily secured between the prepositioned hooks 28 without requiring an undue amount of time. After the ropes or cords 26 have been suspended from the hooks 28, newspapers or rags of a predetermined color are hung from the ropes or cords 26 to further differentiate the safe from the unsafe areas. Thus, the erection of the warning barrier 24 along the perimeter of the safe or protected area 25 utilizing ropes or cords 26 and colored papers or rags 30 provides a quick, convenient, inexpensive method for differentiating the safe from the unsafe areas of a house 10 after a nuclear explosion.

In the typical house, the safe area 25 will include portion of various rooms within the house so that some semblance of normal living may be practiced during the period in which the radiation outside the house is dissipating. Depending on the number of nuclear explosions and the severity of the attack, this period may be days, weeks or months. It is apparent then, that the warning barrier 24 provides a visible physical barrier between the safe and unsafe areas of the house during any length of time after the nuclear explosion.

Although the warning barrier shown in FIGS. 1 and 2 provides sufficient protection from alpha and beta radiation, it is necessary to seek refuge in the cellar or basement area 16 of the typical house 10 in order to escape the hazards of gamma radiation. Although generally gamma radiation is more short-lived than either alpha or beta radiation, it is necessary to leave the confines of the protected area 25 to obtain access to the gamma radiation shelter in the basement. Thus, use of the stairs 18 is required. In such an event, external shielding shown at 32 in FIG. 1 is required to protect the occupants of the house 10 from alpha and beta rays as well as gamma rays while they are moving between the basement area 16 and the protected area in the upper floors 25. Such shielding is preferably placed externally of the house 10 and may be of several available nuclear radiation shielding materials which have been widely publicized for their effectiveness. Of these, lead is probably the best known. Thus, external shielding 32 is used to shield the occupants of the house from gamma rays in all areas where they must pass from the protected basement area 16 to the protected area 25 on the upper floors.

Figure 3:
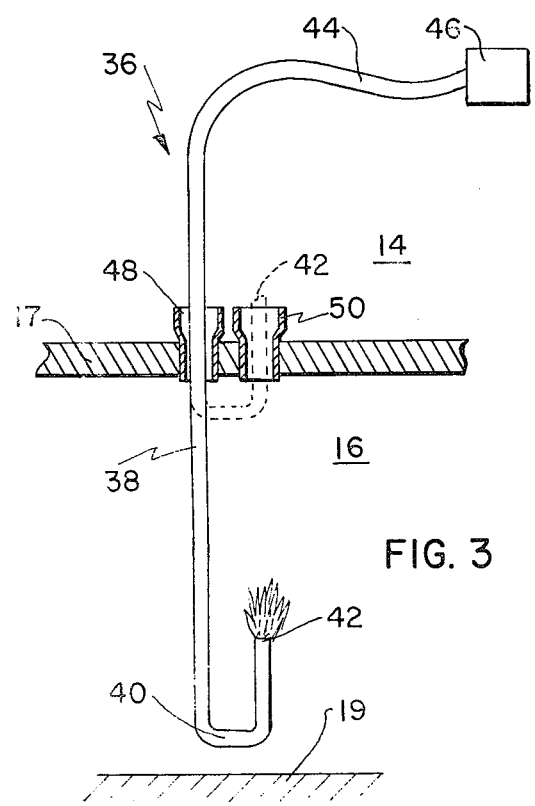
FIG. 3 is a fragmentary, side elevation of one embodiment of the combustion means for determining whether a sufficient amount of oxygen is present in the atmosphere, which combustion means includes means for mounting the apparatus in a floor of the building

Referring now to FIGS. 2 and 3, a means 35 for determining the sufficiency of the oxygen within various areas of the house, particularly the basement, is provided within the safe area 25. Means 35 takes the form in one embodiment of the invention as a movable combustion means 36 as shown in FIG. 3. Combustion means 36 comprises a conduit 38 having one end 40 bent into the shape of a J such that its extreme end 42 is directed vertically upwards. At the other end of the conduit 38 is secured an elongated extension comprising a flexible conduit 44 which is connected to a pressurized source of combustible gas 46. The combustion means 36 is mounted reciprocally through the floor 17 of the typical house 10, which floor separates the upper level 14 from the lower or basement level 16. The combustion means 36 is mounted within a conduit or pipe 48 forming a port or aperture through floor 17 thereby allowing the reciprocal movement of the conduit 38 therethrough. A second port or aperture formed by positioning a second length of pipe or conduit 50 adjacent the first port or aperture 48 may be formed such that when the conduit 38 is drawn all the way up, the end 42 extends through conduit 50, as shown by the phantom lines in FIG. 3. Thus, the gas emerging from end 42 is ignited forming an open flame over end 42. The gas is under sufficient pressure to keep the flame ignited regardless of small air drafts or movements of the conduit 38. Consequently, when the conduit 38 is lowered into the basement atmosphere 16 conduit 50 has the dual purpose of allowing visual observation of the open flame at the end 42 of conduit 38 as the conduit is lowered. It will be apparent that the conduit 38 is long enough to reach near the basement floor 19 as well as intermediate areas between the basement floor and the first floor 17. Accordingly, the atmosphere at all levels therebetween can be checked for the quality of the atmosphere and the sufficiency of the amount of oxygen contained therein all from within the safe area on the first or upper floor level 14 by means of a visual determination through conduit 50. The materials used for conduit 38, flexible conduit 44, conduits 48 and 50 are fireproof materials which are also inexpensive and readily obtainable. Thus, iron or steel pipe as well as fireproof, non-combustible plastic pipe may be used.

Figure 4:
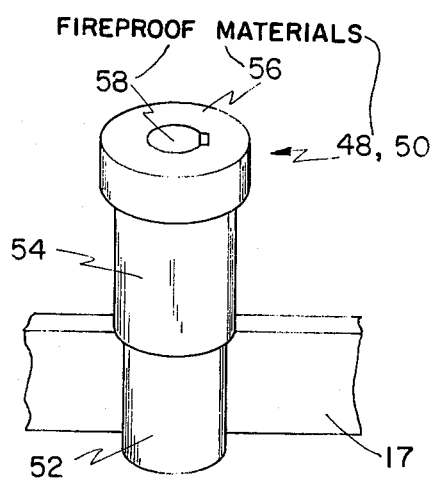
FIG. 4 is a fragmentary, perspective view of the means for mounting the apparatus of FIG. 3 in the floor of a typical housing or dwelling.

As shown in FIG. 4, the conduit or pipes 48 and 50 are normally securely mounted in a floor joist of floor 17. The conduit 48 or 50 includes a section 52 extending through the floor 17 and a section 54 which is slightly larger which extends above the floor 17. A cap or cover 56 is threadably, hingedly or otherwise secured over the open end of section 54 to completely close off the conduit. Cover 56 includes a hinged or otherwise pivotally secured closure means 58 for covering an aperture or slot in cover 56. The closure means 58 may thus be opened to admit the conduit 38 such that the conduit can be lowered into the basement atmosphere in order to check the qualitiy thereof. Therefore, it is not necessary to remove the entire cover 56 to utilize the combustion means 36 described above. Preferably, conduits 48 and 50 are circular in cross section and have diameters somewhat larger than the diamter of conduit 38 thereby allowing easy movement of conduit 38 therethrough.

Figure 5:
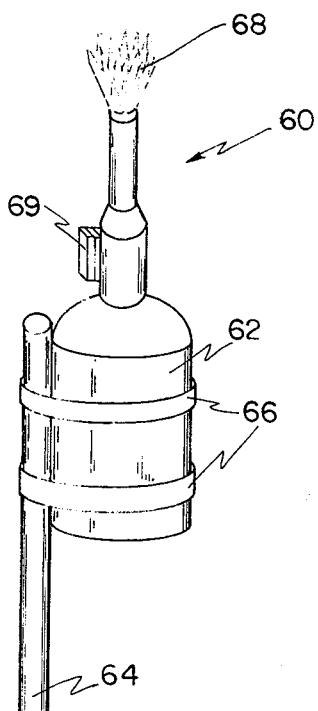
FIG. 5 is a perspective view of another embodiment of the invention comprising a portable combustion means for probing areas of the atmosphere.

Referring now to FIG. 5, a second embodiment 60 of the combustion means for checking the quality of atmosphere in desired areas is shown. As shown therein, combustion means 60 comprises a portable combustion means including a self-contained blowtorch or butane-type torch 62 to which is strapped or otherwise secured an extended handle 64 by means of straps 66. When ignited, the torch 62 has an open flame 68 which is used to check the quality of the atmosphere in various areas. The torch 62 contains a combustible gas, such as butane gas, under pressure such that flame 68 will not be blown out by small drafts or movement of the combustion means 60. Consequently, the only way torch 62 can be extinguished is by the use of control valve 69 or by its emersion in an inferior quality atmosphere. In this connection, it will be understood that an oxygen poor atmosphere such as one produced by the gases resulting after a nuclear explosion in low level areas would not contain sufficient oxygen to either allow the burning of flame 68 on torch 62 or to support human life therein. Consequently, when combustion means 60 is utilized to probe various areas of the atmosphere in low level areas such as basement 16, the quality of the air is determined visually be checking the burning flame 68 in those areas before persons enter those areas. Further, extended handle 64 is utilized by a person descending into such low level areas by means of basement stairs, etc., whereby he can probe the areas he expects to enter before entering those areas. Thus, it is possible for him to determine the quality of the air in all areas before he enters those areas.

Figure 6:
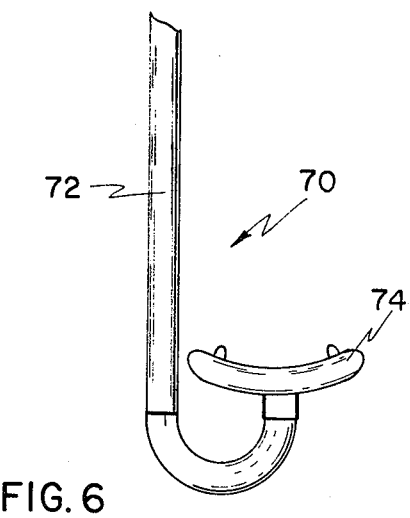
FIG. 6 is a side elevation of a snorkel tube which may be used while probing the various areas of the atmosphere of the building.

As shown in FIG. 6 a snorkel means 70 is comprised of a snorkeling tube 72 and a mouthpiece 74. Snorkel means 70 is utilized by a person using portable combustion means 60. Thus, as the person carrying means 60 walks through the atmosphere to be checked, he uses snorkel means 70 in order to breathe better quality air near the upper areas of the atmosphere to be checked while he is probing the remainder of the atmosphere below the uppermost portions thereof. In this connection, it will be apparent that tube 72 is great enough in length to extend to areas near the ceiling of rooms whose atmospheres are to be checked. Further, it will also be understood that well-known scuba-type diving equipment including self-contained tanks of compressed air (not shown) may be used by a person probing various portions of the atmosphere with combustion means 60.

The method for protecting against nuclear radiation and suffocation following a nuclear explosion in a building having at least two levels will now be apparent. As shown in FIGS. 1 and 2, a safe or protected area 25 is cordoned off within a typical house or dwelling 10 by means of a warning barrier 24 comprising rope or cord 26 suspended between the walls of the house. The safe or protected area 25 is spaced inside the exterior walls of the house a uniform distance represented by "X" in FIGS. 1 and 2 which is beyond the maximum penetration distance for alpha and beta type radiation and also includes a sufficient safety margin. Colored newspapers or rags are hung from ropes 26 to further differentiate the boundary represented by the warning barrier 24. Further, a means for testing and determining the quality of atmosphere in lower levels of the building or house 10 is positioned within the confines of the safe or protected area 25. Such a means is one similar to that shown at 36 in FIG. 3. Combustion means 36 is lowered from the area above the basement level 16 in order to check the atmosphere therein. Basement level 16 is utilized as the protected area from all remaining types of radiation including gamma rays which are highly penetrating and very dangerous to human existence.

A similar but slightly modified method utilizes a portable combustion means such as that shown in FIG. 5 at 60 which is carried by a person desiring to check various areas of the lower level or basement 16. In this connection, the inhabitant of the house 10 would ignite the combustion means 60 and insert it into the atmosphere to be checked from areas outside the atmosphere such as on stairwell 18 by means of the extended handle 64. The extended handle 64 also allows the inhabitant to probe various hard to-get-at places in the basement 16 while walking through the basement. In this latter case a snorkel means such as that shown at 70 or other similar scuba diving equipment utilizing self-contained air tanks is used by the inhabitant to assure a sufficient quantity of oxygen while he is probing the atmosphere.

Therefore, it will be understood that the method and apparatus described herein provide a suitable means for protecting oneself in a typical dwelling structure against nuclear radiation and suffocation after a nuclear explosion. It will be understood that the method and apparatus shown and described provide areas for protection against alpha, beta and gamma radiation as well as providing a means for verifying the condition and quality of the atmosphere in areas to be utilized as radiation shelters. It will also be understood that the method and apparatus may be quickly and conveniently utilized by the average person using inexpensive and readily available materials which normally form a part of the inventory of nearly all households or which are easily obtained at low cost. Thus, the method and apparatus will be available to all persons on an equal basis regardless of their incomes.

While several forms of the invention have been shown and described, other forms will now be apparent to those skilled in the art. Therefore, it will be understood that the embodiments shown in the drawings and described above are merely for illustrative purposes, and are not intended to limit the scope of the invention which is defined by the claims which follow.

The embodiments of the invention in which an exclusive property or privilege is claimed as follows:

1. Apparatus for determining a lack of oxygen within a building having a floor and upper and lower levels above and below said floor respectively and a certain atmosphere within each level comprising a portable combustion means for testing an atmosphere having a flame exposed to said atmosphere; said combustion means including an elongated extension projecting therefrom bent into a J-shape, having a fluid passageway therethrough, and means for passing a combustible gas through said passageway, said J-shaped extension including a vertically upwardly extending opening for emitting said combustible gas upwardly to provide an upwardly extending flame visible from above; and aperture means in said floor for reciprocally raising and lowering said extension in said floor such that said combustion means may be lowered into the atmosphere of said lower level to test the oxygen quality of that atmosphere, said aperture means including a portion allowing ignition of said combustible gas by raising of the portion of said extension including said opening through said floor for said ignition of said combustible gas at said opening whereby, when said extension is lowered into said lower level, said flame will be extinguished if there is sufficient lack of oxygen in said atmosphere of said lower level; said aperture means including a first aperture in which said extension is mounted for reciprocal raising and lowering and a second aperture comprising said portion of said aperture means through which the portion of said extension including said opening is passed for ignition of said flame and through which said flame is observed as said extension is lowered into said lower level atmosphere.

2. Apparatus as described in claim 1 wherein pipes are mounted in said apertures in said floor, said pipes comprising fireproof material and including fireproof covers on the upper ends thereof, said covers each including an aperture and a closure means therein.

3. Apparatus as described in claim 2 wherein said floor is between a basement and first floor level of said building.

4. Apparatus for determining the lack of oxygen in the lower level of a building having at least an upper and lower level and a floor therebetween; said apparatus comprising two apertures formed in said floor, and means for determining a lack of oxygen in an atmosphere; one of said apertures being of sufficient size to allow the oxygen sufficiency determining means to be raised and lowered therethrough into and out of the atmosphere of said lower level; said oxygen sufficiency determining means including upwardly extending means for insertion into said upper level from said lower level through the other of said apertures to initiate operation of said oxygen sufficiently determining means, said other aperture also being sufficiently large to allow the visual observation of said oxygen sufficiency determining means when lowered into said lower level atmosphere for visual determination of the quality of said atmosphere.

5. The apparatus of claim 4 wherein said oxygen sufficiency determining means comprises a combustion means including an open flame; the amount of oxygen in said lower level atmosphere being determined by observing said flame through said other aperture.

6. The apparatus of claim 5 wherein said apertures are immediately adjacent one another, whereby said combustion means can be ignited through said other aperture.

* * * * *

UNITED STATES PATENT AND TRADEMARK OFFICE
CERTIFICATE OF CORRECTION

PATENT NO. : 3,945,800
DATED : March 23, 1976
INVENTOR(S) : Charles J. Roos

It is certified that error appears in the above—identified patent and that said Letters Patent are hereby corrected as shown below:

Column 2, line 41;
    "safter" should be --safer--;
Column 4, line 51;
    "expolsion" should be --explosion--;
Column 4, line 65;
    "portion" should be --portions--;
Column 6, line 48;
    After "burning" insert --of--;
Column 8, line 2;
    After "claimed" insert --are--.

Signed and Sealed this

*twenty-ninth* Day of *June 1976*

[SEAL]

Attest:

RUTH C. MASON
*Attesting Officer*

C. MARSHALL DANN
*Commissioner of Patents and Trademarks*